United States Patent [19]

Sih

[11] Patent Number: 4,855,435
[45] Date of Patent: Aug. 8, 1989

[54] PYRIDYL-SUBSTITUTED BENZOTHIOPHENES

[75] Inventor: John C. Sih, Kalamazoo, Mich.

[73] Assignee: The Upjohn Company, Kalamazoo, Mich.

[21] Appl. No.: 715,595

[22] Filed: Mar. 25, 1985

Related U.S. Application Data

[63] Continuation of Ser. No. 433,940, Oct. 12, 1982, abandoned, which is a continuation-in-part of Ser. No. 385,621, Jun. 8, 1982, abandoned.

[51] Int. Cl.$^4$ .................. C07D 405/06; C07D 405/12
[52] U.S. Cl. .................................... 546/274; 546/269; 546/273
[58] Field of Search ................................ 546/280, 274

[56] References Cited

U.S. PATENT DOCUMENTS

| | | | |
|---|---|---|---|
| 4,112,224 | 9/1978 | Bundy | 542/426 |
| 4,259,338 | 3/1981 | Paioni et al. | 424/267 |

FOREIGN PATENT DOCUMENTS

| | | | |
|---|---|---|---|
| 0050957 | 5/1982 | European Pat. Off. | 546/280 |
| 2537837 | 3/1976 | Fed. Rep. of Germany . | |
| 8034198 | 10/1980 | United Kingdom | 514/342 |

OTHER PUBLICATIONS

D. Harris, et al., Advances in Prostaglandin and Thromboxane Research 6:437 (1980).
T. Miyamoto, et al., Advances in Prostaglandin and Thromboxane Research 6:443 (1980).
H. Tai, et al., Advances in Prostaglandin and Thromboxane Research 6:447 (1980).

*Primary Examiner*—Alan L. Rotman
*Attorney, Agent, or Firm*—Lawrence T. Welch; Donald L. Corneglio

[57] ABSTRACT

The present invention provides novel pyridinyl-benzothiophenes and derivatives thereof which are useful as thromboxane A$_2$ (TXA$_2$) synthetase inhibitors and as such represent potent pharmacological agents.

1 Claim, No Drawings

PYRIDYL-SUBSTITUTED BENZOTHIOPHENES

CROSS REFERENCE TO RELATED APPLICATIONS

This application is a continuation of copending application Ser. No. 433,940 filed 10-12-82 (abandoned), which-in-turn is a continuation-in-part of application Ser. No. 385,621, filed June 8, 1982, (abandoned).

BACKGROUND OF THE INVENTION

The present invention relates to novel compositions of matter. More particularly, the present invention relates to substituted benzothiophenes and derivatives thereof. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researches have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Avances in Prostaglandin and Thromboxane Research, 6: 417 (1980), and references cited therein. Most important are compounds which selectively inhibit $TXA_2$ synthetase. Id.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6: 437 (1980); pyridine and its derivatives, disclosed in T. Miyamoto, et al., Advances in Prostaglandin and Thromoboxane Research, 6: 443 (1980), and British patent application No. 2,039,903A (abstracted in Derwent Farmdoc No. 50111C (1980)). See also H. Tai, et al., Advances in Prostaglandin and Thromboxane Research, 6: 447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

SUMMARY OF THE INVENTION

Thus, the present invention particularly provides: A compound of formula I wherein $Z_1$ is
(a) 4-pyridinyl,
(b) 3-pyridinyl, or
(c) 3-pyridinyl substituted at the 4 position by
 (1) methyl,
 (2) —$OCH_3$,
 (3) —$N(CH_3)_2$, or
 (4) —$NH_2$, or
(d) 3-pyridinyl substituted at the 2, 4, 5, or 6 position by chlorine;

wherein $X_1$ is
(a) —$(CH_2)_n$—,
(b) —O—,
(c) —S—,
(d) —$CH_2$—O—,
(e) —$CH_2$—$NR_3$—,
(f) —$N(R_3)$—$CH_2$—, or
(g) —O—$CH_2$—;

wherein $R_1$ is hydrogen, a pharmacologically acceptable cation, ($C_1$-$C_{12}$) alkyl, ($C_3$-$C_{10}$) cycloalkyl, ($C_7$-$C_{12}$) aralkyl, phenyl, phenyl mono-, di-, or trisubstituted by chloro, ($C_1$-$C_3$) or alkyl, or phenyl para-substituted by
(a) —NHCO—$R_{25}$,
(b) —O—CO—$R_{26}$,
(c) —CO—$R_{24}$,
(d) —O—CO—(p—Ph)—$R_{27}$, or
(e) —CH=N—NH—CO—$NH_2$, wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein —(p—Ph) is 1,4-phenylene;

wherein
$R_7$ is
(a) hydrogen,
(b) —$CH_2OH$,
(c) —$COOR_1$,
(d) —$CH_2N(R_4)_2$,
(e) —CN,
(f) —$CON(R_4)_2$, or
(g) —C(O)—$R_4$;

wherein
$R_3$ is
(a) hydrogen,
(b) ($C_1$-$C_3$)alkyl, or
(c) acyl;

wherein $R_4$ is
(a) hydrogen,
(b) ($C_1$-$C_4$)alkyl, or
(c) phenyl;

wherein $R_9$ and $R_{12}$ are the same or different and are
(a) hydrogen,
(b) ($C_1$-$C_4$)alkyl
(c) fluoro,
(d) chloro,
(e) bromo,
(f) —$OCH_3$, or,
(g) when taken together and attached to contiguous carbon atoms, —O—$CH_2$—O—;

wherein D represents a single or a double bond;
wherein m is an integer of from 0 to 4, inclusive; and
wherein n is an integer of from 2 to 4, inclusive; including, pharmacologically acceptable acid addition salts thereof; and
when D represents a single bond, an enantiomer or a racemic mixture of enantiomers thereof.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cycklopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1PL-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g.,
mono-, di, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as benzothiophenes, using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention are tested for $TXA_2$ inhibition as follows:

Rabbit aortic strips are superfused in series with Krebs solution. Thromboxane $A_2$ ($TXA_2$) is generated by mixing prostaglandin $H_2$ ($PGH_2$) with human platelet microsomes (HPM).

Potential inhibitors are tested by comparing the response of the rabbit aorta to the amount of $TXA_2$ produced by mixing $PGH_2$ and HPM without the test compoound in the reaction medium and then the amount of $TXA_2$ produced when the test compound is added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

The novel compounds of this invention are thus shown to be highly active as selective inhibitors of the thromboxane synthetase enzyme system. Accordingly, these novel comppounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin.

When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already pesent in the gastrointestinal tract. For this purpose, these compounds are injected or infused intravenously, subcutaneously, or intramuscularly in an infusion dose range about 0.1 μg to about 500 μg/kg body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the Amercian Society for Cell Biology, in the Journal of Cell Biology, 87: 64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219: 299 (1981).

The compounds of the present invention are prepared by the methods depicted in Chart A–K.

The benzothiophenes of the present invention are prepared by the method of Chart A. Conversion of the formula LXXXV thiophenol to the formula LXXXVII benzothiophene is accomplished using known methods as described, e.g., in Y. Matsuki, et al., Nippon Kugaku Zasshi 87: 186 (1966) and Chapman, et al., J. Chem. Soc. 514 (1968). The formula LXXXVII benzothiophene thus prepared is carboxylated by known means (e.g., pouring a solution of the LXXXVII compound, in an inert solvent in the presence of n-butyllithium, over crushed dry ice), to yield the formula XCI compound, which is converted to other compounds of this invention by the methods described below.

The compounds of the Formula LXXXV are well known and readily available compounds, and may be prepared from known benzylpyridines of the Formula XX as depicted in Chart B. (See, also, British patent application No. 2,039,903A).

Referring to Chart B, a compound of the Formula XX, wherein all variables are defined as above, is nitrated by methods well known in the art, for example, treatment with nitric acid. (While the para nitro compound is the predominant product, the meta and ortho nitro compounds are also formed in smaller quantities. The desired isomer is separated by known methods.) The nitro function is easily reduced by treatment with hydrogen over a 5% palladium-on-carbon catalyst, to form a Formula XXII amine. This amino group is replaced by a hydroxyl moiety via dizaotization followed by decomposition of the diazonium salt in hot aqueous acid. This phenol is then treated as depicted in Chart K to yield the corresonding thiophenol, which is then converted to the claimed compounds by the method of Chart A.

Compounds of the Formula XX when $X_1$ is —$CH_2N$— may not be readily available. However, compounds of the Formula XXIII when $X_1$ is —$CH_2N$— are disclosed in G. Walker, et al., J. Med. chem. 9: 624 (1966). Formula XX compounds when $X_1$ is —O— are disclosed in F. Villani, et al., J. Med. Chem. 18: 1 (1875). Formula XX compounds when $X_1$ is $(CH_2)_n$ and n is zero are disclosed in A. Katritzky, Chem. Soc. (London) p. 1511 (1960). Formula XX compounds when $X_1$ is —$CH_2O$— are disclosed in British Pat. No. 1,203,149.

Compounds of the Formula XXIII when $X_1$ is —$(CH_2)_n$— and n is 2, 3, or 4 are prepared according to Chart F. A hydroxybenzaldehyde of the Formula LXXI (wherein P is 0, 1, or 2) is reacted with an appropriate pyridinylalkyltriphenylphosphonium chloride of the Formula LXXII in the presence of n-butyllithium to yield the unsaturated hydroxyphenylalkylpyridine of the Formula LXXIII. Catalytic reduction of the olefinic bonds yields the alkylene bridged compounds of the formula LXXIV. Related compounds of the Formula XX wherein m is three are disclosed in F. Villani, et al., J. of Pharm. Sciences, 60: 1586–1587 (1971). Formula XX compounds wherein m is four are disclosed in B. Baker, et al., J. Med. Chem. 14: 793–799 (1971). These compounds are converted to the corresponding thiol by the method of Chart J below.

For compounds wherein m is one, the method of Chart C is used. An ester of the Formula XL is reduced with lithium aluminum hydride in ether or tetrahydrofuran to yield the corresponding alcohol after workup. This alcohol is tosylated or mesylated using p-toluenesulfonyl chloride or methanesulfonyl chloride in pyridine to yield the Formula XLII product. (Ts indicates the tosylated compound, but the compound could also be mesylated). This compound is treated with excess sodium cyanide in dimethylformamide (DMF) and stirred under nitrogen at room temperature for 5 hr to yield the Formula XLIII cyano compound. This compound is dissolved in ethanol and treated with 25% aqueous potassium hydroxide to yield the corresponding acid. This compound is esterified by means well known in the art, e.g., treatment with diazomethane in methanol for the methyl ester. Pharmacologically acceptable salts are also prepared by means well known in the art.

Chart D depicts the synthesis of compounds of the present invention wherein m is 2, 3, or 4. In Chart D, q is zero, one, or 2. An ester of the Formula L is reduced with diisobutylaluminum hydride (DIBAL) in toluene or methylene chloride at low temperature to yield, after workup, the Formula LI aldehyde. Reaction of this aldehyde with an alkoxy alkylene-triphenylphosphorane of the formul $Ph_3P=CHCH_2—(CH_2)_q(COOR_{10}$ (wherein Ph is phenyl) yields the unsaturated ester of the Formula LII after workup. Careful reduction of this unsaturated ester by reaction with one equivalent of hydrogen over palladium-in-carbon in alcohol yields the saturated ester of the Formula LIII. The free acid or a pharmacologically acceptable salt of this ester is prepared by means well known in the art. The corresponding amides, phenacyl esters, and the like are prepared by the methods depicted in e.g., U.S. Pat. Nos. 4,292,445 and 4,172,206.

The dihydrobenzothiophenes are prepared as depicted in Chart E. A solution of a formula LX benzothiophene in water is stirred with excess sodium amalgam (NaHg) for 24 hr. After workup there is obtained the corresponding formula LXI dihydrobenzothiophene. (See, e.g., D. T. Witiak, et al., J. Med. Chem. 14, 754 (1971).)

Reduction of the corresponding acid or ester of the formula $COOR_{10}$ with lithium aluminum hydride as depicted in Chart C, (XL to XLI) is used to prepare all of the corresponding alcohols within the scope of Formula I.

Compounds of this invention werein $X_1$ is —O— or —S— are prepared by the method of Chart H. In Chart I, $X_5$ is —S— or —O—, and is attached at the 3 L or 4 position of the pyridine ring. This procedure is described more fully in Preparations A-30 through A-34 and Examples A-35-38. A compound of the formula LXXX (e.g., 3-hydroxypyridine) is treated with potassium hydroxide, and reacted with a compound of the formula LXXXI (e.g., p-bromoanisole) in the presence of activated copper bronze to yield the formula LXXXII product. The formula LXXXII compound is then reacted with hydrogen bromide to yield the formula LXXXIII product, which is then transformed to the corresponding benzofuran final products by the methods of Charts A, B, C, D, E, F, and H. The LXXXIII compounds wherein $X_5$ is —S— are similarly prepared by reaction of a 3 or 4-bromopyridine (LXXX') with p-methoxythiophenol (LXXXI) to yield the formula LXXXII compound, which is converted to the thiol by the method of Chart J, below.

Chart G depicts another method for preparing the compounds of this invention. The formula XCVIII compound, prepared by the methods depicted in Chart A, is reacted with 3-amino pyridine to yield the compound of the formula C wherein $X_1$ is —NH—. Reaction of the formula XCVIII compound with 3-lithiopyridine (prepared, e.g., by reaction of 3-bromopyridine with n-butyllithium) yields the formula CI compound wherein $X_1$ is —C(OH)—. The formula XCVII compound is also treated with a mixture of sodium hydride, dimethylformamide, and 3-hydroxypyridine to obtain the formula CII compound wherein $X_1$ is —O—.

Chart I depicts a method for preparing chloro-pyridinyl compounds of this invention. The CV pyridinyl derivative is treated with m-chloroperbenzoic acid to yield the corresponding CVI N-oxide. The N-oxide is treated with phosphorous oxychloride to yield the corresponding chloropyridyl isomers of the formula CVII.

Substituted benzothiophenes (i.e. compounds wherein $R_9$ and $R_{12}$ are other than hydrogen) are prepared by the methods depicted in Charts J and K.

Chart J depicts a method for preparing methyl or methoxy substituted benzothiophenes. In Chart J, $R_{19}$ is methyl or methoxy. The formula CXV ether is hydrolyzed (using hydrobromic acid for example) to yield the formula CXVI alcohol. Similaly, the formula CXV' ether is hydrogenolyzed with hydrogen over palladium on carbon catalyst to yield the formula CXVI alcohol. This alcohol is treated as in Chart K to yield the corresponding thiol, which is converted to the compounds of this invention by the method of Chart A.

Chart K depicts a general method for preparing the substituted benzothiophenes used in the method of Chart A. The $R_9$ and $R_{12}$ substituted para-methylthiophenyl starting materials of the formula CXXXI are thus prepared by conversion of an appropriate formula CXXX substituted phenol into a thiophenol using the well established Newman-Kwart rearrangement (see, e.g., Org. Syn., 51: 139 (1971)) and other related procedures. See also the Schönberg rearrangement by J. L. Wardell in "The Chemistry of the Thiol Group", ed. S. Patai, Wiley, N.Y., 1974, p. 163 and the Kawata-Harano-Taguchi rearrangement, Chem. Pharm. Bull.

(Japan), 21, 604 (1973). The paramethylphenols are either commercially available or can be prepared by methods known in the art.

Similarly, various substituted hydroxy benzaldehydes are available commercially or may be prepared by methods known in the art. The hydroxybenzaldehydes are thus converted to the claimed benzofurans by the method of Charts K and A, as described above.

Compounds where $Z_1$ is 4-methylpyridine are prepared by converting the corresponding 4-chloropyridine of Chart H with methyl magnesium halides to the 4-methyl pyridine derivative according to the procedure described in K. Thomas and D. Jerchel, in "Newer Methods of Organic Chemistry," Vol. III., W. Foerst, ed., Academic Press, N.Y. 1964, pp 74–75.

The 4-methoxy, 4-amino, and 4-N,N-demethylamino derivatives are prepared from the corresponding 4-methoxy-3-bromopyridine (see T. Talik, Roczniki Chem, 36: 1465 (1962)), 3-bromo-4-aminopyridine (see T. Talik, Roczniki Chem., 37: 69 (1963)) and 3-bromo-4-dimethylaminopyridine (see J. M. Essery and K. Schofield, J. Chem. Soc., 4953 (1960)), respectively, using the procedures of Chart F (conversion of XCVIII to CI).

Preparation of various other benzothiophene derivatives within the scope of this invention are prepared by analogous procedures well known in the art.

Certain compounds of the present invention are preferred. Thus, compounds of the formula I, wherein D denotes a double bond, $X_1$ is —$(CH_2)_n$— (wherein n is zero or one, more preferably one), $Z_1$ is 3-pyridinyl, m is zero, $R_7$ is $COOR_1$, $R_1$ is Na or H and $R_9$ and $R_{12}$ are hydrogen are preferred. Compounds having all these preferences are more preferred. Thus, 5-(3-pyridinylmethyl)-benzo[b]thiophene-2-carboxylic acid is the most preferred compound of this invention.

DESCRIPTION OF THE PREFERRED EMBODIMENTS

The present invention is seen more fully by the Examples given below.

Preparation 1 p-(3-pyridinyloxa)phenylthioacetaldehyde diethyl acetal

Refer to Chart A (conversion of LXXV to LXXXVI where $Z_1$ is 3-pyridinyl and $X_1$ is oxygen).

Using the procedure described in Chapman, et al., J. Chem. Soc. 514 (1968), and starting with p-(3-pyridinyloxa)thiophenol, the titled compound is prepared.

Preparation 2

5-(3-Pyridinyloxa)-benzo[b]thiophene

Refer to Chart A (conversion of LXXXVI to LXXXVII).

Using the procedures of Chapman, et al., J. Chem. Soc. 514 (1968), and starting with Preparation 1, the titled compound is prepared.

EXAMPLE 3

5-(3-pyridinyloxa)-benzo[b]thiophene-2-carboxylic acid, sodium salt (Formula I: $Z_1$ is 3-pyridinyl, $X_1$ is oxygen, $R_9$ and $R_{12}$ are hydrogen, m is zero and D is a double bond)

Refer to Chart A (conversion of LXXXVII to XCI).

To a magnetically stirred solution of the compound of Preparation 2 (0.74 g) in about 30 ml of tetrahydrofuran is added 1 equivalent of 1.6M n-BuLi in hexane. The solution is stirred for 1 hr at 25° C. The contents were diluted with 25 ml of 1N NaOH and washed with ether. The aqueous solution was acidified to pH 5 with 2N KHSO4 and thoroughly extracted with chloroform. Concentration of the solvent in vacuo afforded the free acid, which was directly saponified in 5 ml of methanol using 1 equivalent of 1N NaOH. After complete hydrolysis, the resulting solution is freeze-dried to afford about 70 mg of the sodium salt.

EXAMPLE 4

5-(3-Pyridinyloxa)-2-hydroxymethylbenzo[b]thiophene (Formula I: $Z_1$ is 3-pyridinyl, $X_1$ is oxygen, $R_9$ and $R_{12}$ are hydrogen, m is zero and D is a double bond).

Refer to Chart C (conversion of XL to XLI).

To a magnetically stirred suspension of lithium aluminum hydride (2–3 equivalents) in tetrahydrofuran is added at 25° C. a solution of the free acid obtained in Example 3, in tetrahydrofuran (0.5M). After complete reaction, the titled compound is obtained after normal workup.

TABLE I

FORMULA

I

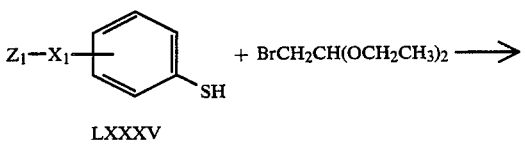

CHART A

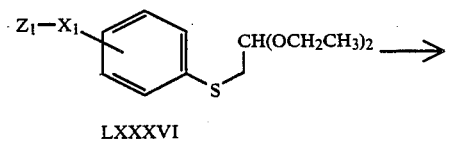

LXXXV

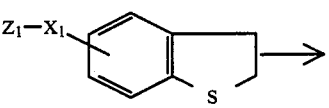

LXXXVI

LXXXVII

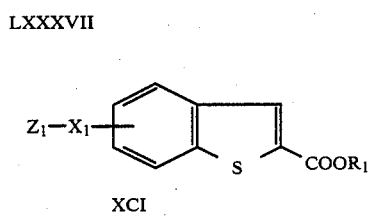

XCI

CHART B
XX
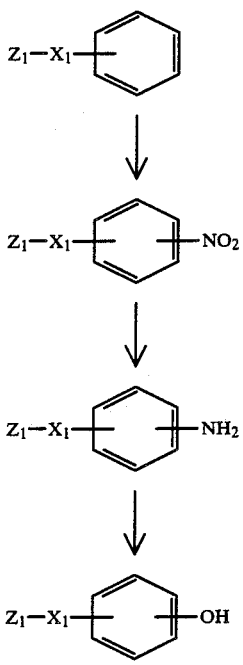
CHART D -continued
LI, LII, LIII, LX
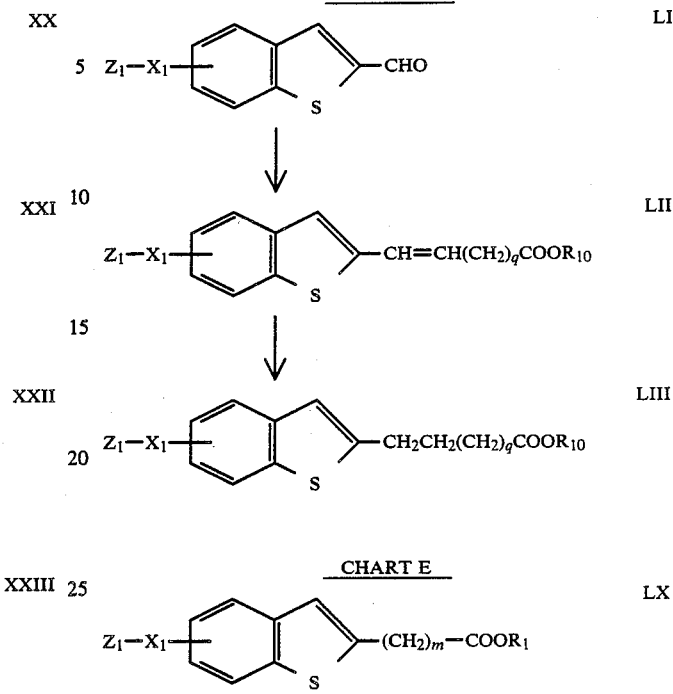
CHART C
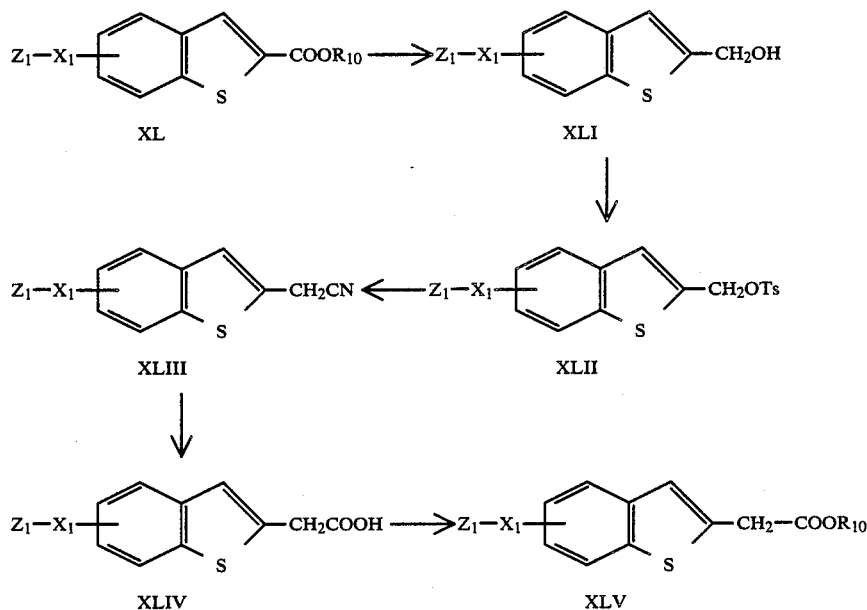
CHART D
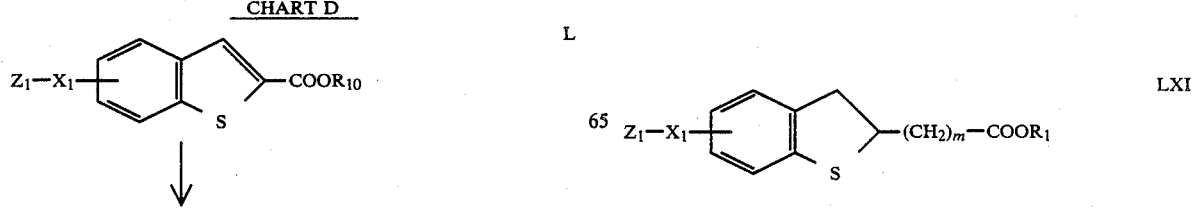
L, LXI

CHART F
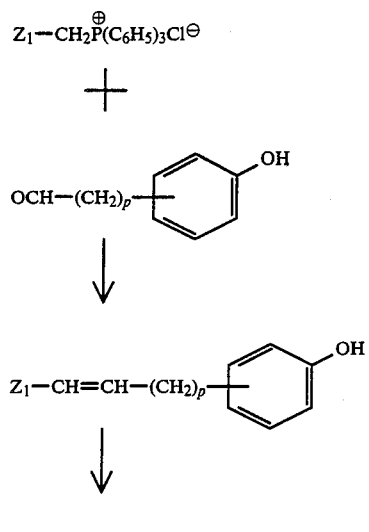
CHART G
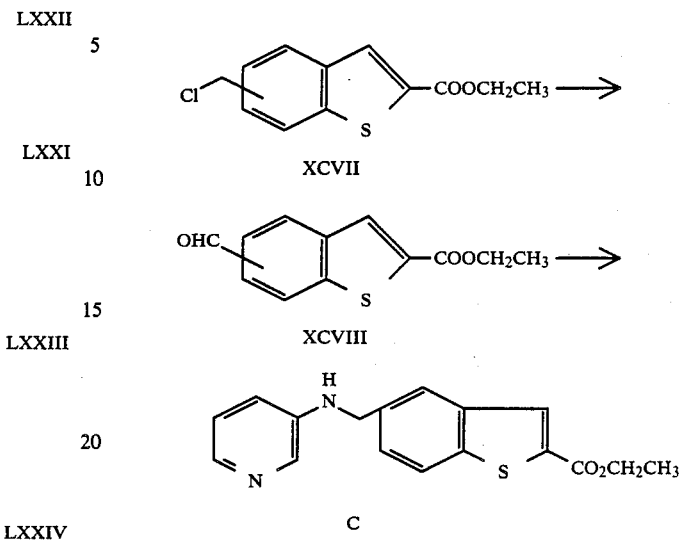
CHART H
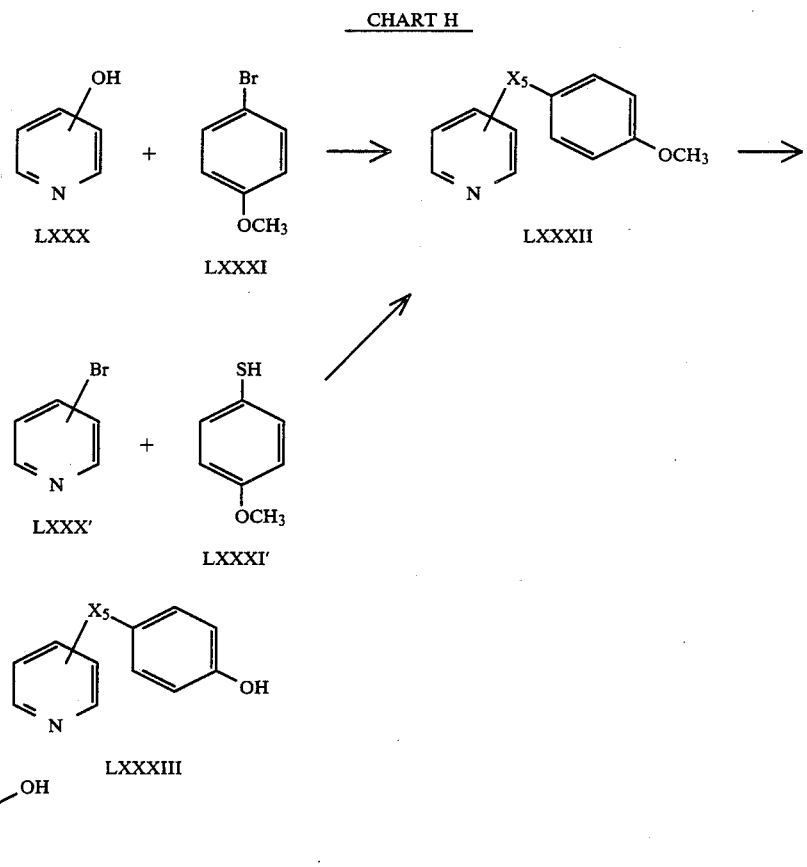
CHART G
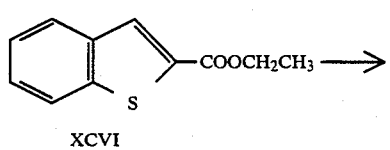
CHART I
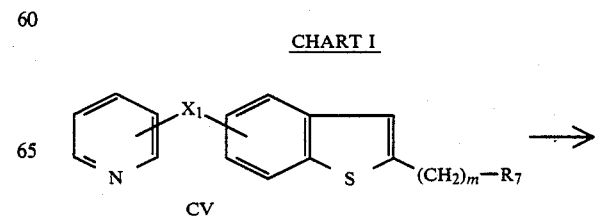

CHART I
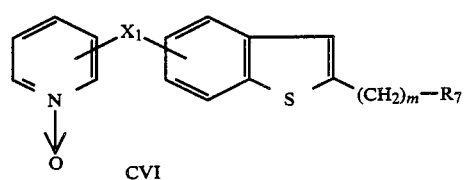
CVI
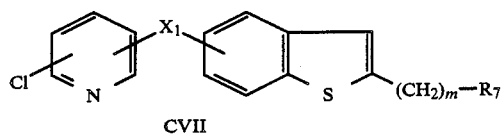
CVII
CHART J
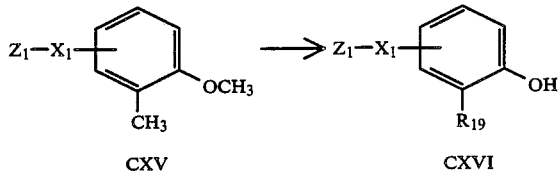
CXV CXVI
CHART J (continued)
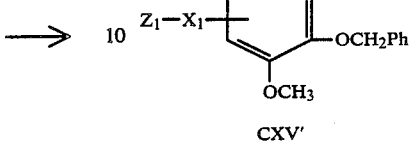 
CXV'
CHART K
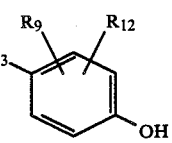
CXXX CXXXI
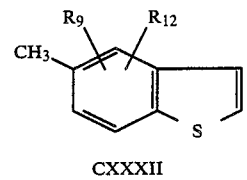
CXXXII
I claim:
1. A compound consisting of 5-(3-Pyridinyloxa)-2-hydroxymethylbenzo(b)thiophene including pharmacologically acceptable acid addition salts thereof.
* * * * *